United States Patent [19]
Kenley et al.

[11] Patent Number: 5,932,103
[45] Date of Patent: Aug. 3, 1999

[54] WITHDRAWAL OF PRIMING FLUID FROM EXTRACORPOREAL CIRCUIT OF HEMODIALYSIS MACHINES OR THE LIKE

[75] Inventors: Rodney S. Kenley, Libertyville; Christine F. Schroeder, Gurnee, both of Ill.

[73] Assignee: Aksys, Ltd., Lincolnshire, Ill.

[21] Appl. No.: 08/938,111

[22] Filed: Sep. 26, 1997

Related U.S. Application Data

[60] Continuation-in-part of application No. 08/560,043, Feb. 16, 1996, abandoned, which is a division of application No. 08/388,275, Feb. 13, 1995, Pat. No. 5,591,344.

[51] Int. Cl.$^6$ .......................... B01D 61/24; B01D 61/28; B01D 61/32; A61M 1/14
[52] U.S. Cl. .......................... 210/646; 210/85; 210/108; 210/134; 210/143; 210/258; 210/321.69; 210/411; 210/645; 210/647; 604/4
[58] Field of Search .............................. 210/85, 108, 134, 210/136, 143, 411, 252, 258, 645, 646, 647, 739, 321.69; 604/4, 5, 6

[56] References Cited

U.S. PATENT DOCUMENTS

| | | | |
|---|---|---|---|
| 5,110,477 | 5/1992 | Howard et al. | 210/647 |
| 5,336,165 | 8/1994 | Twardowski | 210/646 |
| 5,484,397 | 1/1996 | Twardowski | 604/5 |
| 5,776,345 | 7/1998 | Truitt et al. | 210/645 |

FOREIGN PATENT DOCUMENTS

| | | |
|---|---|---|
| 3443744 | 6/1986 | Germany . |
| WO 9625214 | 8/1996 | WIPO . |

*Primary Examiner*—John Kim
*Attorney, Agent, or Firm*—McDonnell Boehnen Hulbert & Berghoff

[57] ABSTRACT

A method for withdrawing priming fluid from the extracorporeal circuit of a dialysis machine is described which substantially prevents return of the priming fluid back to the patient. In accordance with the method, priming fluid is drawn from the extracorporeal circuit through the dialyzer membrane and into the dialysate circuit. Blood is introduced into the extracorporeal circuit as the priming fluid is withdrawn through the dialyzer. Withdrawal of the priming fluid may be accomplished by pumping the blood pump in the forward direction at a first rate and operating a pump in the dialysate circuit at a second rate. Valves in the dialysate circuit are operated such that the pump in the dialysate circuit draws priming fluid across the dialyzer membrane into the dialysate circuit, and thereby prevents the priming fluid from being returned to the patient. In a preferred embodiment, the fluid volumes of the arterial and venous portions of the extracorporeal circuit, and the fluid volume of the blood side of the dialyzer, are known in advance. With this information, it is possible to operate the blood and dialysate pumps such that the blood progresses into the arterial and venous lines at different rates such that blood reaches the dialyzer via both lines at about the same time, while at the same time the priming fluid is withdrawn through the dialyzer. Thus, in this embodiment, blood fills the extracorporeal circuit after priming with only a small amount of priming fluid remaining in the blood compartment of the dialyzer being returned to the patient.

23 Claims, 2 Drawing Sheets

WITHDRAWAL OF PRIMING FLUID FROM EXTRACORPOREAL CIRCUIT OF HEMODIALYSIS MACHINES OR THE LIKE

CROSS-REFERENCE TO RELATED APPLICATION

This is a continuation-in-part of application of Rodney S. Kenley et al., Ser. No.: 08/560,043, filed Feb. 16, 1996, abandoned, which is a division of application of Rodney S. Kenley et al., Ser. No. 08/388,275 filed Feb. 13, 1995, now U.S. Pat. No. 5,591,344.

BACKGROUND OF THE INVENTION

A. Field of the Invention

This invention relates to dialysis machines, and more particularly to hemodialysis machines that have an extracorporeal blood circuit in which a priming fluid is circulated through the extracorporeal circuit. The priming fluid is used to remove air bubbles and manufacturing-related contaminants contained within the blood tubing set and blood side of the dialyzer prior to the introduction of the patient's blood into the machine. The invention could be practiced in other similar types of machines, such as a liver dialysis machine.

B. Description of Related Art

Hemodialysis machines are used for treating patients with inadequate kidney function. Hemodialysis machines include, among other things, an extracorporeal blood circuit typically comprising an arterial line, a blood pump, a dialyzer and a venous line. Blood is removed from the patient via the arterial line and pumped by the blood pump to the dialyzer, where blood-borne toxins and excess fluids are removed from the patient's blood. The blood is then returned to the patient via the venous line.

It is known in the art to prime the extracorporeal circuit prior to the dialysis session to remove air and residual contaminants from the blood tubing set and blood side of the dialyzer. The priming fluid is typically a physiologic solution such as either a dialysate solution or a saline solution. In the prior art, the priming solution is returned to the patient via the venous line when blood is introduced into the arterial line. Alternatively, as the blood is introduced into the arterial line, the venous line is held over a receptacle such as bucket and the priming fluid is emptied into the receptacle exterior of the extracorporeal circuit. Both of these approaches have disadvantages. Returning the fluid to the patient compounds the patient's need to have fluid removed from the patient and prolongs, for many patients, the time required for dialysis. Dumping the priming fluid into a receptacle presents an obvious disposal and inconvenience problem, as well as the potential for contamination of the venous line connector and other sanitary problems since the operator will typically have to handle the venous line connector when the priming fluid is being disposed of in the receptacle.

The present invention avoids the above difficulties by providing a method of removing the priming fluid from the extracorporeal circuit that can prevent the priming fluid from being returned to the patient, without requiring any external receptacles to receive the priming fluid, and without exposing the venous lines or the patient to additional risks of contamination, such as may occur by the patient's hands or clothing coming into contact with the connectors terminating the blood tubing set.

SUMMARY OF THE INVENTION

A method is provided for removing a priming fluid from an extracorporeal circuit of a dialysis machine. The extracorporeal circuit comprises arterial and venous lines that are filled with the priming fluid immediately before the patient's blood is introduced into the extracorporeal circuit. A dialyzer is connected to the arterial and venous lines which has a membrane separating the extracorporeal circuit from a dialysate circuit. In accordance with the method, at least a portion of the priming fluid from the extracorporeal circuit is transported across the dialyzer membrane into the dialysate circuit. Simultaneous with the transporting of the priming fluid out of the extracorporeal circuit, blood from the patient is introduced into one of the arterial and venous lines as the priming fluid is being transported across the dialyzer membrane. Thus, in accordance with the invention, the withdrawal of the priming fluid from the extracorporeal circuit by transportation into the dialysate circuit prevents the priming fluid from being substantially returned to the patient. The invention also prevents the priming fluid from being disposed of in a receptacle external of the extracorporeal circuit.

The portion of priming fluid that is transported across the dialyzer membrane may vary, depending on the needs of the patient, the calibration of the pumps and other components that are used to transport the priming fluid, and other factors. In a preferred embodiment, at least 50 percent of the priming fluid in the extracorporeal circuit is transported across the dialyzer membrane, and about 90 percent or more may be removed in many instances, particularly in a dialysis regimen in which excess water is being removed from the patient.

In a preferred embodiment, as the priming fluid is removed, blood from the patient is introduced into both the arterial and venous lines so as to fill the arterial and venous lines as the priming fluid is transported across the dialyzer membrane. The blood fills the arterial and venous lines and meets at the dialyzer as substantially all of the priming fluid is removed from the extracorporeal circuit.

In another aspect of the invention, the priming fluid is transported across the dialyzer membrane with a blood pump in the extracorporeal circuit and a pump in the dialysate circuit (such as a dialysate pump or an ultrafiltration pump as described in detail below). The arterial line and venous line each have a known predetermined fluid volume, and the blood side or compartment of the dialyzer also has a known predetermined volume. With this information known, the blood pump and a pump in the dialysate circuit may be operated at predetermined flow rates for a predetermined amount of time based on the fluid volumes of the arterial line, venous line, and blood side of the dialyzer in order to fill the arterial and venous lines simultaneously with blood as the priming fluid is withdrawn from the extracorporeal circuit.

In a preferred embodiment, the blood pump flow rate (BPF) and dialysate-side pump flow rates (DPF) are determined according to the relationship:

$$\frac{BPF}{DPF - BPF} = \frac{\text{arterial line volume} + \text{blood side of dialyzer volume}}{\text{venous line volume}}.$$

When the pumps are operated in this manner, the blood reaches the dialyzer via the arterial and venous lines at roughly the same time, providing for the removal of the substantial majority (and up to approximately 90 percent or more in many cases) of the priming fluid in the extracorporeal circuit.

In a preferred aspect of the invention the dialysis machine includes a computer control system having a memory storing a table of at least one commercially available dialyzer for installation into the extracorporeal circuit. Each of the commercially available dialyzers have a blood side and a predetermined fluid volume of the blood side of the dialyzer, which is stored in memory. The computer control system controls the blood pump and the pump in the dialysate circuit based on the particular fluid volume of the commercially available dialyzer installed in the extracorporeal circuit in accordance with the table stored in memory. This enables the computer control system to operate the blood and dialysate pumps in a manner such that a controlled amount of priming fluid is removed from the extracorporeal circuit, such as substantially all the priming fluid, and leave the extracorporeal circuit filled with blood when dialysis commences.

An additional advantage is that a small amount of priming fluid may be left in the extracorporeal circuit so as to not hemoconcentrate the blood, which can promote clotting. This feature is best accomplished in a system in which the volumes of the blood compartment of the dialyzer and arterial and venous tubing sets are known and stored in memory, which enable the blood pump and the pump in the dialysate side to be operated with precision to effect the proper amount of withdrawal of priming solution.

These and many more features, advantages of the invention will be apparent from the following detailed description of preferred embodiment of the invention.

BRIEF DESCRIPTION OF THE DRAWINGS

In the following detailed description of presently preferred and alternative embodiments of the invention, reference will be made to the accompanying drawing figures, in which like reference numerals refer to like elements in the various views, and in which.

DETAILED DESCRIPTION OF THE PREFERRED EMBODIMENT

Figure 1:
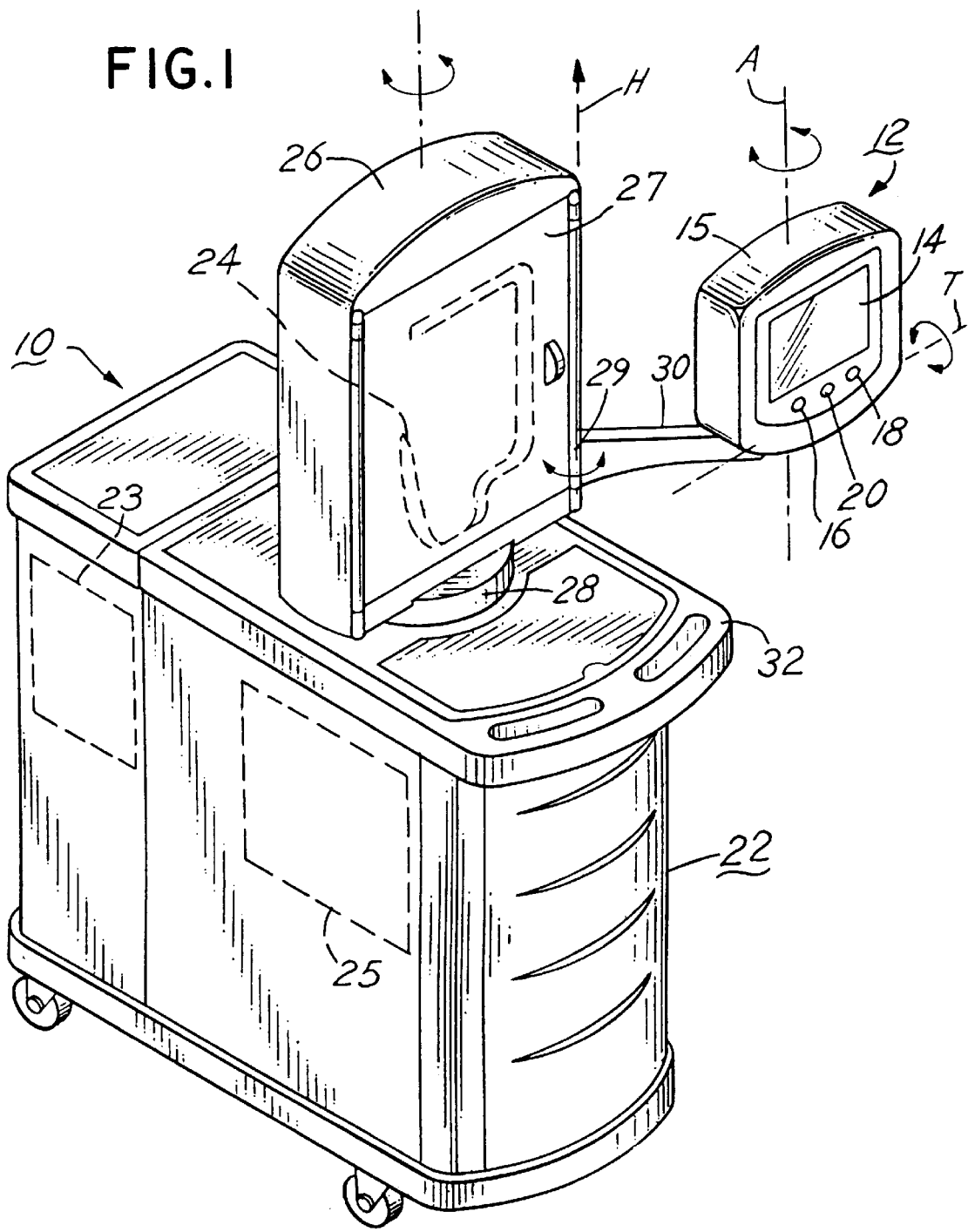
FIG. 1 is an illustration of a dialysis machine, including an extracorporeal circuit and user interface, which may be employed in practicing the invention.

FIG. 1 is an illustration of a dialysis machine 10 having a user interface 12 which may be employed in practicing the invention. The dialysis machine 10 in the illustrated embodiment is a machine suitable for use outside of a traditional dialysis clinic setting, such as the home, nursing home or self-care clinic environment, however the invention is not considered limited to such a machine. Before discussing the priming fluid withdrawal invention in detail, a brief discussion of the dialysis machine 10 of FIG. 1 and some of the features related to the present invention will be set forth.

The dialysis machine 10 includes an extracorporeal circuit 24 mounted above a lower cabinet 22. The extracorporeal circuit is housed behind a door 27 in an enclosure 26 that is mounted to a turntable 28. The turntable 28 is moveably mounted to the top of the lower cabinet 22 such that the turntable 28, enclosure 26 and extracorporeal circuit 24 are capable of rotation as a unit relative to the lower cabinet 22 about a vertical axis.

The dialysis machine 10 has a water treatment module 23 and a dialysate preparation module 25 contained within a lower compartment or cabinet 22. The water treatment module 23 plays no part in the present invention, and is described in detail in U.S. Pat. No. 5,591,344 to Kenley et al. and assigned to Aksys, Ltd., the assignee of the present invention. The Kenley et al. U.S. Pat. No. 5,591,344 is incorporated by reference herein. Additionally, the manner in which the dialysate solutions are prepared in the dialysate preparation module 25 and circulated through a dialysate circuit to a dialyzer in the extracorporeal circuit in the enclosure 26 is not particularly important to this invention and is well known in the art, and may be as described in the Kenley et al. patent (a preferred embodiment), or otherwise. A preferred embodiment of a dialysate preparation module having the ability to withdraw priming fluid from the extracorporeal circuit is described in detail below.

The details as to the user interface 12 are also not particularly important insofar as the present invention is concerned, and may be as described in U.S. Pat. No. 5,788,851, issued to Rodney S. Kenley, et al. or as described in the Grogan et al. patent, U.S. Pat. No. 5,326,476 or otherwise. The user interface includes a touch sensitive display screen 14 and a set of three hard keys 16, 18 and 20 that are pressed by the user to enter and change parameter values and information for the machine. The user interface is connected via a hinge 29 and arm 39 to the cabinet 26. The user interface rotates about a tilt axis T and a vertical axis A so as to enable the user interface to be positioned at a location convenient for the patient. The user interface may also be mounted to the front corner 32 of the machine.

Figure 2:
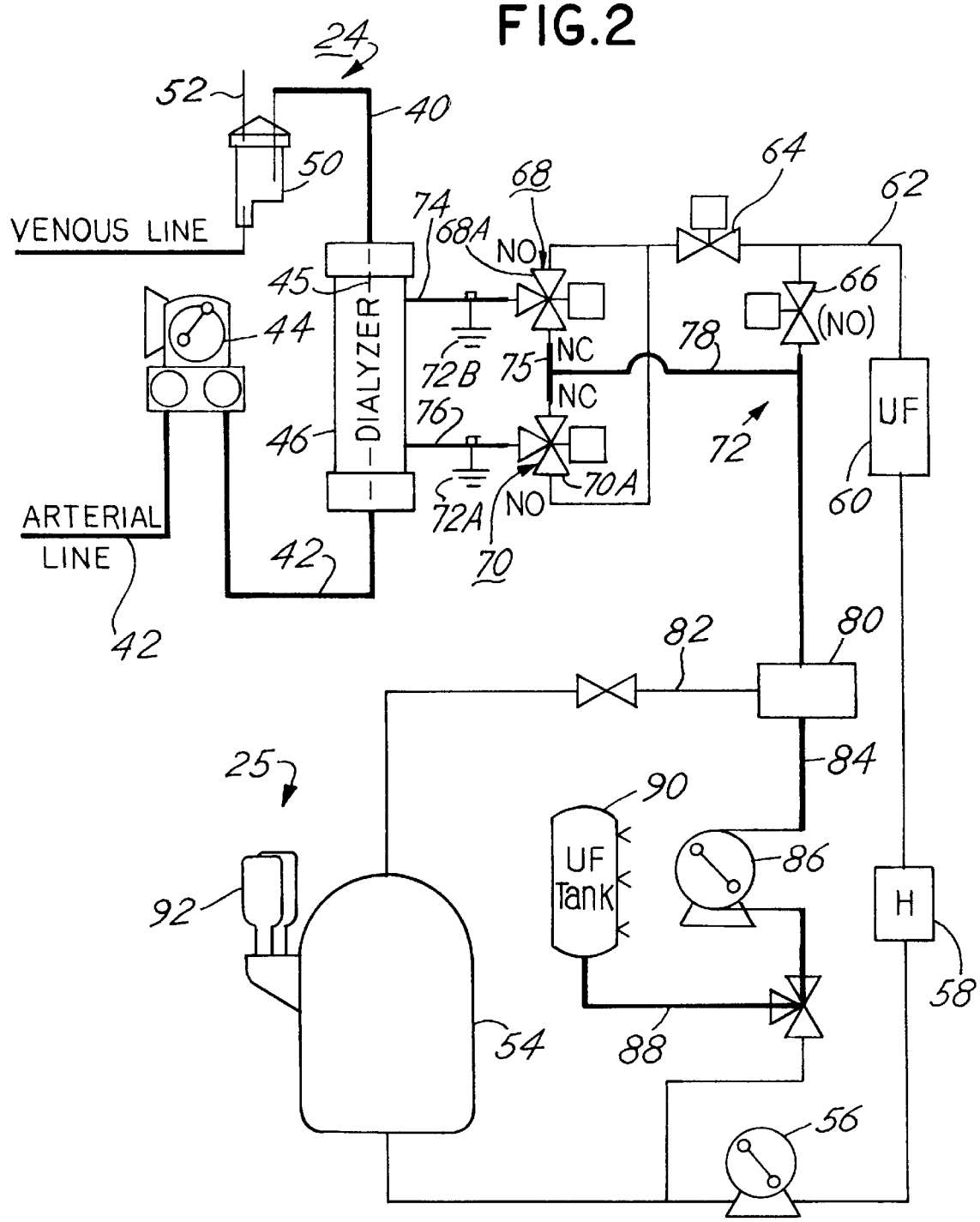
FIG. 2 is a schematic diagram of a representative extracorporeal blood circuit and dialysate circuit of the machine of FIG. 1, with the components thereof not related to the present priming withdrawal invention omitted for the sake of conciseness and clarity.

FIG. 2 is a schematic illustration of the extracorporeal circuit 24 and dialysate preparation system 25 of the machine 10 of FIG. 1. In the embodiment of FIG. 2, blood is removed from the patient and introduced into the arterial line 42, and pumped by a blood pump 44 to the blood compartment or blood side of a dialyzer 46. Blood-borne toxins and excess water are removed from the blood through the membrane 45 of the dialyzer 46 into a dialysate circuit 72, and the blood is returned to the patient via the venous line 40. To prevent air from being introduced into the blood being returned to the patient, it is conventional in the dialysis art to place the air trap 50 in the venous line. The fluid level in the air trap 50 can be adjusted by known methods, and in FIG. 2 air is pumped into or out of the air trap 50 via line 52 to raise or lower the level in the air trap.

Further details of the particular extracorporeal circuit illustrated in FIG. 2 are not considered to be pertinent to the operation of the present invention, and can be found in the published PCT application of Kenley et al., publication no. WO 96/25214, or in the patent to Kenley et al. U.S. Pat. No. 5,591,344.

The dialysate preparation module 25 includes a fifty liter dialysate tank 54 storing a batch quantity of dialysate solution, and a pump 56 for pumping the solution from the tank through a heater assembly 58, a sterile ultrafilter 60, and into a line 62 leading to the dialysate side of the dialyzer 46. An inlet valve 64, bypass valve 66 and first and second inlet and outlet three way valves 68 and 70 are provided in the dialysate circuit 72. The dialysate circuit 72 includes an inlet line 74 and outlet line 76 from the dialyzer. The outlet line 76 is connected via valve 70 to a dialysate outlet line 78 that leads to a manifold 80. Valves downstream of the manifold 80 dictate whether the returning dialysate is directed to the tank 54 via line 82, or sent via line 84 to an ultrafiltration pump 86. The ultrafiltration pump 86 operates to remove precise volumes of dialysate solution from the dialysate circuit 72 into an ultrafiltration tank 90 via line 88. During the dialysis session, the fluid removed from the patient is pumped by the ultrafiltration pump from the dialysate circuit into the ultrafiltration tank 90, enabling precise measurement of the volume of fluid removed from the patient.

In the illustrated embodiment, dialysate solution is prepared in the tank 54 as a result of mixing chemicals from vessels 92 that are introduced into the tank with reverse osmosis water from the water preparation module 23 of FIG. 1. The details are not considered pertinent and are described in the above-referenced Kenley et al. '344 patent. The particular details as to the dialysate preparation module, the manner in which the dialysate solution is prepared and circulated, are not considered to be a part of the invention and can be by any of several other known methods, such as using proportioning systems, such as described in the Grogan et al. patent, or otherwise.

Prior to the initiation of a dialysis session, the extracorporeal circuit 24 must be primed with a physiologic fluid. Saline solution could be used for this purpose, and introduced into the arterial line 42 from a saline bag via a Y-connector in the arterial line and pumped through the extracorporeal circuit with the blood pump. Alternatively, a dialysate solution could be used for this purpose in the manner described in the above-referenced Kenley et al. '344 patent or in the patent to Zbylut Twardowski, M.D., U.S. Pat. No. 5,336,165, which is also incorporated by reference herein. The particular manner in which the extracorporeal circuit is primed is not considered crucial. At the end of the priming process, the extracorporeal circuit 24 is filled completely with the priming fluid, and the patient is connected to the arterial and venous lines 42 and 40 of the extracorporeal circuit. A dialysate solution is prepared in the dialysate preparation module 25 and circulated through the dialysate circuit 72 to the dialyzer 46. The dialysate circuit 72 is completely filled with the dialysate solution.

In the prior art, the priming fluid was either returned to the patient via the venous line 40 (and therefore increasing the amount of fluid that needs to be removed from the patient), or disposed of by the operator holding the venous line 40 connector at the end thereof over a receptacle external of the extracorporeal circuit and drawing blood into the extracorporeal circuit, with the introduction of the blood forcing the priming fluid out of the venous line and into the receptacle.

The present invention contemplates removing at least a portion of the priming fluid from the extracorporeal circuit 24 by transporting the priming fluid through the dialyzer 46 membrane 45 into the dialysate circuit 72. At the beginning of the process, the patient has connected the connectors at the end of the arterial and venous lines to the patient's fistula needles (or central venous catheter) and the extracorporeal circuit is filled with the priming fluid. Simultaneously, the blood from the patient is introduced into at least one of the arterial and venous lines 42, 40 as the priming fluid is being transported across the dialyzer membrane 45. The introduction of the blood into the arterial and/or venous lines 42, 40 and withdrawal of the priming fluid from the extracorporeal circuit 24 into the dialysate circuit 72 prevents the portion of priming fluid transported across the dialyzer from being returned to the patient or disposed of in a receptacle externally of the extracorporeal circuit.

In one preferred embodiment, the blood is introduced into the arterial and venous lines 42 and 40 both at the same time and drawn towards the dialyzer 46. At the same time, as the blood is moving up the arterial and venous lines 42 and 40, the priming fluid is drawn through the dialyzer membrane 45 into the dialysate circuit. The amount of priming fluid that is removed from the extracorporeal circuit can vary in accordance with the invention, depending on such factors as the need of a particular patient to have fluid removed, the accuracy of the calibration of the blood pump 44 and the pump in the dialysate-side (e.g. ultrafiltration pump 86), and other factors. For a typical patient in which a substantial amount of fluid needs to be removed from the patient during the treatment session, it is preferable that at least 50 percent of the priming fluid is transported across the dialyzer membrane 45 into the dialysate circuit 72. With many patients, it is expected that a substantial majority (i.e., greater than 90 percent) of the priming fluid will be advantageously removed. In the later instance, the blood from the patient is introduced into both the arterial and venous lines 42 and 40, respectively, so as to substantially fill the arterial and venous lines 42 and 40 with blood as the priming fluid is transported across the dialyzer membrane 45, such that, at the end of the process of the removing the priming fluid, on the order of 10 percent or less of the total priming fluid in the extracorporeal circuit 24 remains in the blood compartment of the dialyzer 46, with the arterial line 42 and venous line 40 are filled with blood.

The withdrawal of the priming fluid through the dialyzer is preferably accomplished by the operation of the blood pump 44 to pump the patient's blood into the arterial line of extracorporeal circuit 24, and creating a pressure differential at the dialyzer membrane 45 with a pump in the dialysate circuit 72 so as to draw the priming fluid across the dialyzer membrane 45 and into the dialysate circuit. The ultrafiltration pump 86 or dialysate pump 56 of FIG. 2 could be used for this purpose, creating negative pressure in line 78. We have found it more preferable in the illustrated embodiment of FIG. 2 to operate the valves in the dialysate circuit and the ultrafiltration pump 86 in the forward direction to draw priming fluid across the membrane 45 into lines 74 and 76, and pump fluid in line 78 through the manifold 80 into lines 84 and 88 and into the ultrafiltration tank 90. Valve 68 is operated such that normally open port 68A is closed, normally open port 70A of valve 70 is closed, thereby directing the priming fluid from lines 74 and 76 into line 78, with bypass valve 66 closed. The action of the ultrafiltration pump 86 creates a negative pressure at the dialyzer membrane 45 to pull the priming fluid through the arterial and venous lines into the dialysate circuit 72. Valve 64 is also closed so that when the priming fluid is first drawn through line 74 (with valve 70 back to the normally open state) no fluid is pulled from line 62. When the priming fluid is removed from the arterial line, valve 70 is closed such that blood is not drawn through line 76 and the remaining priming fluid in the venous line and blood compartment of the dialyzer is drawn through line 74 only.

The present inventors have appreciated that this priming withdrawal technique can by performed with a substantial amount of precision or control over the precise amount of fluid removed from the extracorporeal circuit 24. The operation of blood pump and ultrafiltration pump is preferably controlled by a software program running in the dialysis machine central computer system, with the software program associated with a memory storing certain machine parameters. Preferably, these parameters include a table storing the fluid volumes of the arterial line and the venous line (including the volume of the air trap at a predetermined fill level). Additionally, the memory stores the fluid volume of the blood chamber of a plurality of commercially available dialyzers that would be installed in the dialysis machine. When the fluid volume of the arterial and venous blood tubing set and blood compartment of the dialyzer are known, it is possible to operate the blood pump 44 and the ultrafiltration pump 86 at predetermined rates for a predetermined amount of time to remove a precise amount of the priming fluid (such as 50 percent, 65 percent or 90 percent). This is because particular flow rates of the pumps 44 and 86 translates into precise quantities of fluid removal across the dialyzer 46 and such rates can be calculated accurately when the volumes of the arterial and venous blood tubing set, drip chamber 50 and blood compartment of the dialyzer 46 are known.

In a preferred form of the invention, the blood pump 44 flow rate (BPF) and dialysate-side pump (86 or 56) flow rates (DPF) having the following relation $$\frac{BPF}{DPF - BPF} = \frac{\text{arterial line volume} + \text{blood side of dialyzer volume}}{\text{venous line volume}} \quad (1)$$

which results in the arterial and venous lines substantially filling with blood completely at approximately the same time, with the priming fluid filling these lines being substantially completely transported across the dialyzer membrane into the dialysate circuit. Representative numbers for the pertinent volumes of an extracorporeal circuit, blood pump flow rate and ultrafiltration pump rate are provided in the table below.

In the above embodiment in which 90 percent or more of the priming fluid is removed from the extracorporeal circuit and the volume of the venous line 40 is greater than the volume of the arterial line 42, typically the blood in the arterial line will reach the dialyzer slightly before the blood in the venous line reaches the dialyzer. This will be known from the above relation (1) and the arterial line volume divided by the blood pump speed. When the blood reaches the arterial header of the dialyzer 46, valve 70 operates to close port 70A and shut off line 76. The remaining priming solution in the venous line is withdrawn through line 74 and connecting line 75. It may be advantageous to leave a small amount of the priming solution in the blood compartment of the dialyzer to avoid hemoconcentration upon the initiation of dialysis and return of blood to the patient.

From the above relation (1), it will thus be observed that the withdrawal of the priming solution is accomplished by operating the blood pump 44 and the pump 86 in the dialysate circuit at predetermined flow rates for a predetermined amount of time based on the fluid volumes of the arterial line, venous line, and blood side of the dialyzer in order to control the volume of fluid removed. It will be apparent that, by reducing the amount of time the pumps operate, less fluid is removed from the extracorporeal circuit, and that by programming the duration of operation of the blood and ultrafiltration pumps precise control is

TABLE 1

| Arterial BTS Volume | Venous BTS Vol. (85% of air trap) | Dialyzer Volume | Dialyzer type | Total (mL) | UFP rate (mL/min) | time for prime (sec) | BLP rate (mL/min) |
| --- | --- | --- | --- | --- | --- | --- | --- |
| 40 | 54 | 110 | F80A | 204 | 150 | 81.6 | 110.29 |
| 40 | 54 | 82 | F60A | 176 | 150 | 70.4 | 103.98 |
| 40 | 54 | 63 | F50A | 157 | 150 | 62.8 | 98.41 |
| 40 | 54 | 42 | F40A | 136 | 150 | 54.4 | 90.44 |
| 40 | 54 | 109 | BellcoBLS 819 | 203 | 150 | 81.2 | 110.10 |
| 40 | 54 | 85 | Nissho PES-150 | 179 | 150 | 71.6 | 104.75 |
| 40 | 54 | 88 | Terumo | 182 | 150 | 72.8 | 105.49 |
| 40 | 54 | 14 | SAMPLE | 108 | 150 | 43.2 | 75.00 |

Note that in the table, the amount of time the ultrafiltration pump and blood pump run at the designated pump rate controls the volume of priming fluid removed from the extracorporeal circuit. For most patients, the amount of time is selected so as to remove at least 90 percent of the priming fluid from the arterial and venous lines.

Note also from the Table that pump rates and times are given for a plurality of commercially available dialyzers that could potentially be used with the machine. The dialysis machine of FIG. 1 may be installed in a clinic, nursing home, self-care center or the home environment. The dialysis machine computer control system has a memory storing a table of a plurality of commercially available dialyzers for installation into the extracorporeal circuit, each of the commercially available dialyzers having a blood side and a predetermined known fluid volume of the blood side of the dialyzers. The user operates the user interface of FIG. 1 to enter the brand and model number of the dialyzer from an approved list, and the computer responsively retrieves this information when the priming removal step is being performed. The computer control system operates the blood pump and a pump in the dialysate circuit (such as ultrafiltration pump 86 or dialysate pump 56) based on the particular commercially available dialyzer installed in the extracorporeal circuit in accordance with the table stored in said memory and relation (1) so as to transport a predetermined amount of the priming fluid across the dialyzer membrane into the dialysate circuit, such as 50 or 90 percent.

achieved. To assist in the precise control, it may be desirable or even required to calibrate the blood pump and the pumps 56 or 86 on a regular basis with a flow meter or other means so that the time of operation of the pumps at the designated flow rates produces the desired quantities of removal of the priming solution.

The fluid that is drawn by the ultrafiltration pump 86 is directed into the ultrafiltration tank 90 in the illustrated embodiment, and typically will be a dialysate solution if the fluid volume of the tubing between the ultrafiltration tank and dialyzer is greater than the fluid volume of the extracorporeal circuit. The particular destination for the priming fluid (or, equivalently, dialysate solution commensurate therewith) is essentially irrelevant. For example, it could be directed to a drain. By directing the fluid into the ultrafiltration tank 90, the fluid can be used for other purposes, such as adjusting the transmembrane pressure in the dialyzer during dialysis, or returning this fluid to the patient in the case where they become quickly hypotensive, or backflushing the fluid across the dialyzer membrane to prevent clot formation.

Persons of skill in the art will appreciate that variations may be made to the preferred and alternative embodiments described above without departure from the true spirit and scope of the invention. For example, the pump 56 in the dialysate circuit could be operated to draw fluid through the dialyzer membrane. The particular details as to the valve arrangement in the dialysate circuit 72 is not considered critical. Additionally, the invention may be practiced in other types of systems, such as a machine for performing liver dialysis or in a hemoconentrator type of system. This true spirit and scope is determined by the appended claims, to be interpreted in light of the foregoing.

We claim:

1. A method of removing a priming fluid from an extracorporeal circuit of a dialysis machine, said extracorporeal circuit comprising arterial and venous lines filled with said priming fluid and a dialyzer connected to said arterial and venous lines, said dialyzer having a membrane separating said extracorporeal circuit from a dialysate circuit and a blood side in said extracorporeal circuit and a dialysate side in said dialysate circuit, the method comprising the steps of:

transporting at least a portion of said priming fluid from said extracorporeal circuit across said dialyzer membrane into said dialysate circuit; and simultaneously introducing blood from a patient connected to said arterial and venous lines into at least one of said arterial and venous lines as said priming fluid is being transported across said dialyzer membrane, whereby the introduction of said blood into said arterial and venous lines and withdrawal of said priming fluid from said extracorporeal circuit prevents said portion of priming fluid from being substantially returned to said patient or disposed of in a receptacle externally of the extracorporeal circuit.

2. The method of claim 1, wherein said at least a portion of said priming fluid comprises at least 50 percent of the fluid volume of said extracorporeal circuit.

3. The method of clam 1, wherein said at least a portion of said priming fluid comprises at least 90 percent of the fluid volume of said extracorporeal circuit.

4. The method of claim 1, wherein the blood from said patient is introduced into both said arterial and venous lines so as to fill said arterial and venous lines as said portion of priming fluid is transported across said dialyzer membrane.

5. The method of claim 1, wherein said extracorporeal circuit further comprises a blood pump and said dialysate circuit comprises a pump in said dialysate circuit, and wherein the method further comprises the steps of:

operating said blood pump to pump blood into the extracorporeal circuit, and creating a pressure differential at the dialyzer membrane in combination with operating said pump in said dialysate circuit so as to draw said priming fluid across said dialyzer membrane.

6. The method of claim 1, wherein said extracorporeal circuit further comprises a blood pump and said dialysate circuit comprises a pump in said dialysate circuit, said arterial line and said venous line each have a known predetermined fluid volume, and wherein said blood side of said dialyzer has a known predetermined volume, and wherein the method further comprises the step of:

operating said blood pump and said pump in said dialysate circuit at predetermined flow rates for a predetermined amount of time based on the fluid volumes of said arterial line, venous line, and blood side of said dialyzer.

7. The method of claim 6, wherein said predetermined flow rates comprise a blood pump flow rate and a dialysate-side pump flow rate, and wherein said blood pump flow rate (BPF) and dialysate-side pump flow rates (DPF) are determined according to the relationship:

$$\frac{BPF}{DPF-BPF} = \frac{\text{arterial line volume} + \text{blood side of dialyzer volume}}{\text{venous line volume}}.$$

8. The method of claim 6, wherein said predetermined amount of time is selected so as to remove at least 90 percent of the priming fluid from said arterial and venous lines.

9. The method of claim 1, wherein said dialysis machine further comprises a computer control system having a memory storing a table of at least one commercially available dialyzer for installation into said extracorporeal circuit, each of said commercially available dialyzers having a blood side and a predetermined fluid volume of said blood side of said dialyzers, and wherein said computer control system operates a blood pump in said extracorporeal circuit and a pump in said dialysate circuit based on the particular commercially available dialyzer installed in said extracorporeal circuit in accordance with said table stored in said memory so as to control the withdrawal of said priming fluid across said dialyzer membrane into said dialysate circuit.

10. The method of claim 9, wherein said blood pump and said pump in said dialysate circuit are operated so as to transport at least 90 percent of said priming fluid across said dialyzer.

11. The method of claim 9, wherein said arterial line and said venous line each have a known predetermined fluid volume, and wherein said blood side of said dialyzer has a known predetermined volume, and wherein the method further comprises the step of operating said blood pump and said pump in said dialysate circuit at predetermined flow rates for predetermined amount of time based on the fluid volumes of said arterial line, venous line, and blood side of said dialyzer.

12. A dialysis machine having an extracorporeal circuit which prevents priming fluid from substantially being returned to a patient connected to said dialysis machine via arterial and venous lines, comprising:

a blood pump in said extracorporeal circuit for circulating fluid in said extracorporeal circuit;

a dialyzer separating said extracorporeal circuit from a dialysate circuit, said dialyzer having a dialyzer membrane with a blood side thereof in said extracorporeal circuit and a dialysate side in said dialysate circuit;

a pump in said dialysate circuit in fluid communication with said dialyzer;

first and second valves in said dialysate circuit positioned upstream and downstream from said dialyzer, respectively; and a computer control system operative of said blood pump, pump in said dialysate circuit and said first and second valves, wherein when said extracorporeal circuit is filled with said priming fluid and a patient is connected to said arterial and venous lines, said computer control system operates said blood pump so as to pump blood into said extracorporeal circuit and said pump in said dialysate circuit and said first and second valves for a predetermined amount of time so as to transport said priming fluid across said dialyzer membrane into said dialysate circuit.

13. The dialysis machine of claim 12, wherein said dialysis machine further comprises an ultrafiltration tank for storing ultrafiltrate from a patient connected to said dialysis machine, and wherein a volume of fluid in said dialysate circuit commensurate with the volume of priming fluid transported across said dialyzer is transported into said ultrafiltration tank as said priming fluid is transported across said dialyzer.

14. The dialysis machine of claim 13, wherein said volume of fluid is pumped into said ultrafiltration tank by an ultrafiltration pump.

15. The dialysis machine of claim 13, wherein said arterial line and said venous line each have a known predetermined fluid volume, and wherein said blood side of said dialyzer has a known predetermined volume, and wherein said computer control system operates said blood pump and said pump in said dialysate circuit at predetermined flow rates for predetermined amount of time based on the fluid volumes of said arterial line, venous line, and blood side of said dialyzer.

16. The dialysis machine of claim 15, wherein said predetermined flow rates comprise a blood pump flow rate and a dialysate-side pump flow rate, and wherein said blood pump flow rate (BPF) and dialysate-side pump flow rates (DPF) are determined according to the relationship:

$$\frac{BPF}{DPF - BPF} = \frac{\text{arterial line volume} + \text{blood side of dialyzer volume}}{\text{venous line volume}}.$$

17. The dialysis machine of claim 12, wherein said predetermined amount of time is selected so as to remove at least 90 percent of the priming fluid from said arterial and venous lines.

18. The dialysis machine of claim 15, wherein said dialysis machine further comprises a computer control system having a memory storing a table of at least one commercially available dialyzer for installation into said extracorporeal circuit, each of said commercially available dialyzers having a blood side and a predetermined fluid volume of said blood side of said dialyzers, and wherein said computer control system operates said blood pump and said pump in said dialysate circuit based on the particular commercially available dialyzer installed in said extracorporeal circuit in accordance with said table stored in said memory.

19. The dialysis machine of claim 13, wherein said volume of fluid stored in said ultrafiltration tank is back-flushed into said extracorporeal circuit during a dialysis session with said machine.

20. The dialysis machine of claim 13, wherein said volume of fluid stored in said ultrafiltration tank is used to adjust the transmembrane pressure of said dialyzer either before or during a dialysis session with said dialysis machine.

21. The dialysis machine of claim 12, wherein said control system is operative of said blood pump and said pump and said first and second valves in said dialysate circuit so as remove a substantial majority of priming fluid from said extracorporeal circuit, while retaining a quantity of said priming solution in said blood side of said dialyzer so as to prevent hemoconcentration of blood being returned to said patient upon the initiation of dialysis.

22. The method of claim 1, wherein said method is performed in a machine for treating a patient suffering from inadequate liver function.

23. The method of claim 1, wherein said method is performed in a machine for treating a patient suffering from inadequate kidney function.

* * * * *